United States Patent [19]
Shiber

[11] Patent Number: 5,192,268
[45] Date of Patent: Mar. 9, 1993

[54] FLEXIBLE THROMBECTOMY SYSTEM
[76] Inventor: Samuel Shiber, P.O. Box 1366, Atkinson, N.H. 03811
[21] Appl. No.: 722,126
[22] Filed: Jun. 27, 1991
[51] Int. Cl.⁵ .............................................. A61B 17/22
[52] U.S. Cl. .................................... 604/53; 606/159; 128/758; 128/749
[58] Field of Search ................. 606/159, 194; 604/22, 604/35, 52, 53, 164, 170, 180, 280, 311, 313, 316; 128/749, 751, 752, 757, 758

[56] References Cited
U.S. PATENT DOCUMENTS

| | | | |
|---|---|---|---|
| 3,438,366 | 4/1969 | Kariher et al. | 128/757 |
| 3,783,998 | 1/1974 | Brush et al. | 128/749 |
| 4,636,199 | 1/1987 | Victor | 604/164 |
| 4,662,376 | 5/1987 | Belanger | 604/22 |
| 4,712,536 | 12/1987 | Hawks | 128/750 |
| 4,808,158 | 2/1989 | Kreuzer et al. | 604/170 |
| 5,011,488 | 4/1991 | Ginsburg | 606/159 |
| 5,011,490 | 4/1991 | Fischell et al. | 606/159 |
| 5,069,224 | 12/1991 | Zinnanti, Jr. | 128/752 |
| 5,092,839 | 3/1992 | Kipperman | 606/194 |

FOREIGN PATENT DOCUMENTS

| | | | |
|---|---|---|---|
| 0291170 | 11/1988 | European Pat. Off. | 606/159 |
| 856788 | 11/1952 | Fed. Rep. of Germany | 604/313 |
| 2602414 | 2/1988 | France | 128/757 |

Primary Examiner—Stephen C. Pellegrino
Assistant Examiner—Ralph A. Lewis
Attorney, Agent, or Firm—Samuel Shiber

[57] ABSTRACT

A flexible thrombectomy system insertable into a patient's blood vessel for sucking and removing a thrombus, comprising in combination, a flexible piston, slidably disposed in a flexible catheter and adapted to be retracted into it, thereby sucking the thrombus into the system.

5 Claims, 2 Drawing Sheets

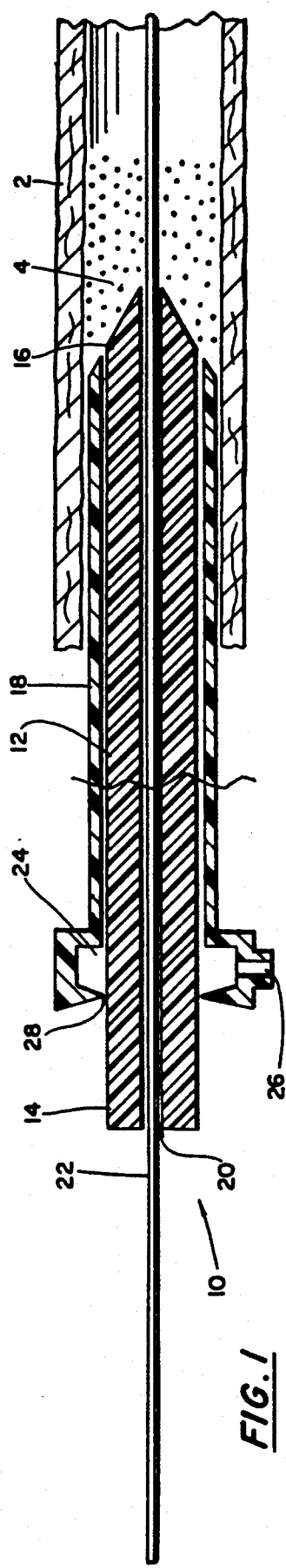
FIG.1
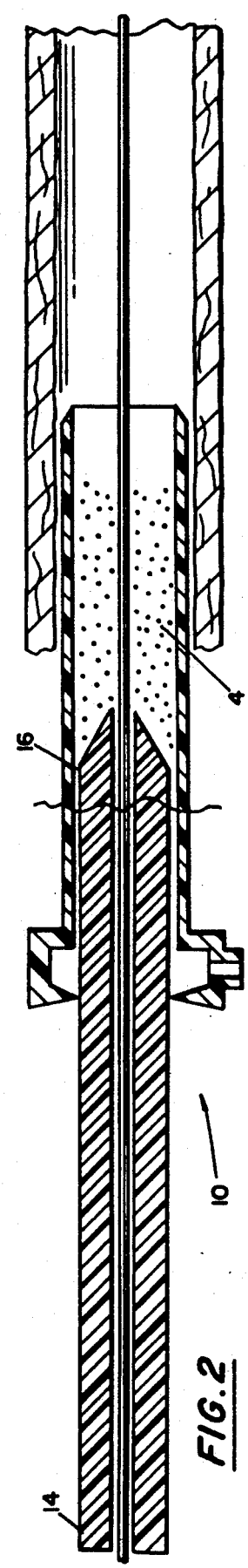
FIG.2
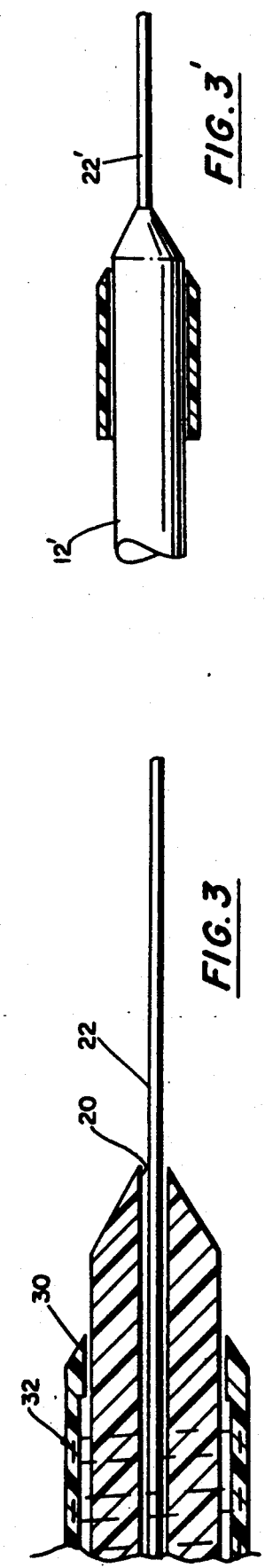
FIG.3
FIG.3'

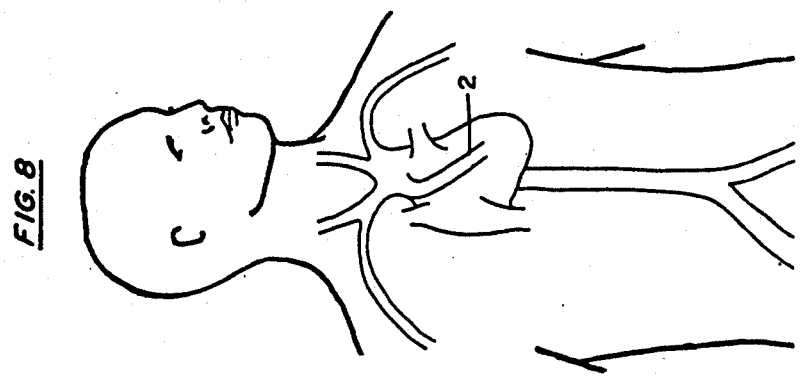
FIG. 8
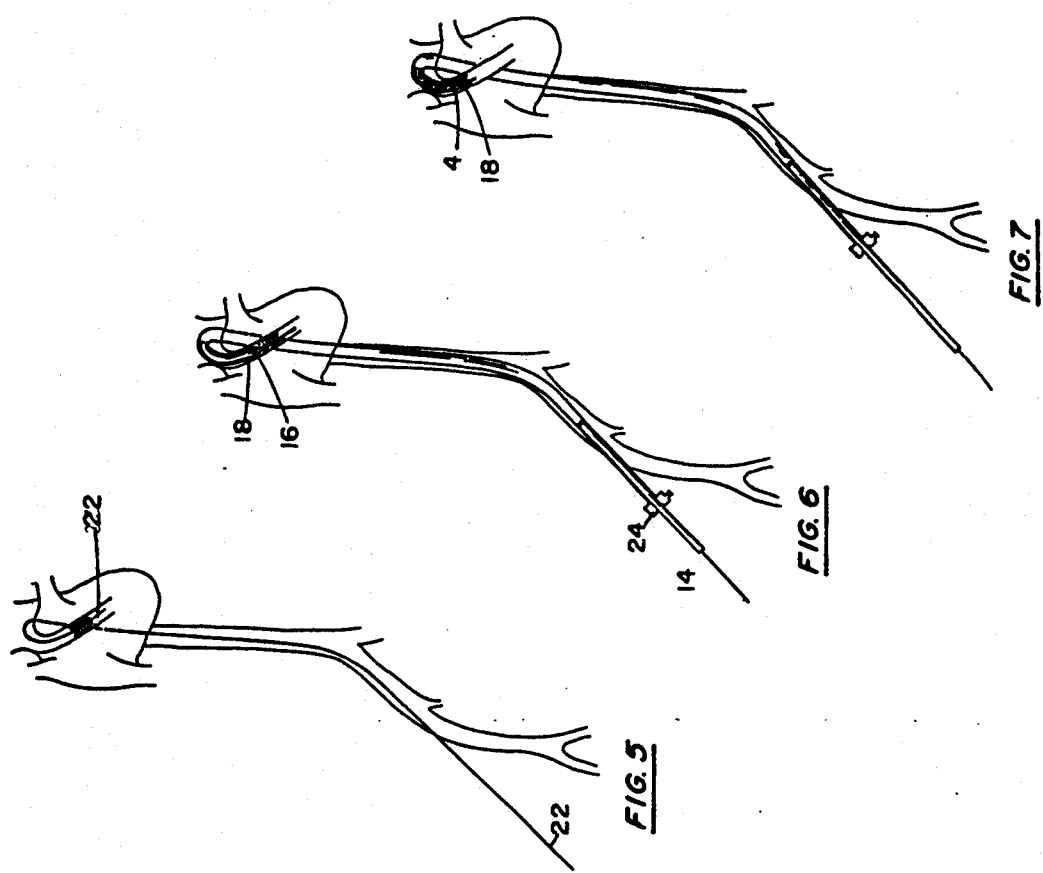
FIG. 7
FIG. 6
FIG. 5
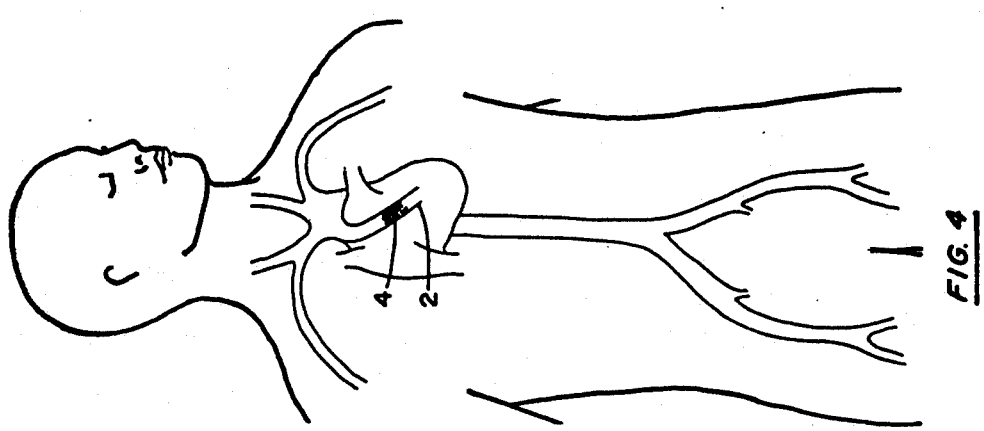
FIG. 4

FLEXIBLE THROMBECTOMY SYSTEM

BACKGROUND AND SUMMARY OF THE INVENTION

A thrombus (blood clot) forming in a blood vessel is often an aggregation of blood elements such as platlets, fibrin and cellular elements. When an artery becomes blocked by a thrombus it leads to ischemic necrosis of the starved tissue, and when it occurs in an artery serving a critical organ, like for example, the heart or the brain, it may lead to severe injury or death.

The objective of the present invention is to provide a method for quickly removing a thrombus and a simple system to do so. The thrombectomy catheter system is insertable into blood vessels, preferably over a flexible guide-wire (guidewire insertion into a vessel is a common standard procedure) and it is made of a flexible catheter and a flexible piston, slidable therein. To operate, the distal end of the system is brought to the immediate vicinity of the thrombus and then the piston is quickly withdraw into the catheter, creating instantaneous pressure drop at its distal tip. The suddenness of the drop in pressure at the distal tip of the system helps to dislodge and suck the thrombus into the system for subsequent withdrawal out of the artery. In contrast, when a physician tries to suck a thrombus into a catheter by applying suction to the catheter's proximal end, the corresponding pressure dorp at the distal end appears dampened, and any flow through the catheter causes a substantial losses along the catheter, reducing the further the negative pressure at catheter's distal end.

The system's elements are shaped so that they are not likely to injure the vessel, especially since the system has to be brought to the vicinity of the thrombus but does not have to be forced across it. The above and other advantages of the invention will become apparent from the following discussion and the accompanying drawings.

BRIEF DESCRIPTION OF THE FIGURES

FIG. 1 shows a general cross sectional view of a flexible thrombectomy system having a flexible piston slidably disposed in a flexible catheter, in a thrombosed blood vessel. The central portion of the flexible thrombectomy system, marked by the heavy break line, has been omitted due to space limitations on the drawing sheet.

FIG. 2 shows a general cross sectional view of the flexible thrombectomy system of FIG. 1 after its piston after has been retracted and the trombus has been sucked into the flexible catheter. As in FIG. 1, the central portion of the flexible thrombectomy system, marked by the heavy break line, has been omitted due to space limitations on the drawing sheet.

FIG. 3 shows a cross sectional view of a modified embodiment of the flexible thrombectomy system having an integral valve means at the distal tip area and a reinforced flexible catheter.

FIG. 3' shows a cross sectional view of a modified embodiment of the flexible thrombectomy system having an integral guidewire means at the distal tip area of the flexible piston.

FIG. 4 schematically shows a thrombosed coronary artery in a patient.

FIG. 5 schematically shows a guidewire inserted at the patient's groin area and threaded through the vasculature into the thrombosed coronary artery.

FIG. 6 schematically shows the flexible catheter containing the flexible piston inserted over the guidewire and into the thrombosed coronary artery.

FIG. 7 schematically shows the flexible piston retracted in the flexible catheter into which the thrombus has been sucked.

FIG. 8 schematically shows a the cleared coronary artery after the system, containing the thrombus, has been withdrawn from the patient.

DETAILED DESCRIPTION OF THE DRAWINGS

Similar parts will be indicated by same numerals throughout the FIGS.

The flexible thrombectomy system comprises elongated parts in a nested relationship. Their ends are referred to as "distal" meaning the end which goes into the vessel and "proximal" meaning the other end. Thus, "distal direction" or "distally" indicates a general direction from the proximal end to the distal end, and "proximal direction" or "proximally" indicates an opposite direction.

FIG. 1 shows a flexible thrombectomy system 10 comprising a flexible piston 12, having proximal and distal ends 14 and 16, respectively, which is slidably disposed in a flexible catheter 18, also having proximal and distal ends.

The piston defines a longitudinal channel 20 in which a flexible guidewire 22 is slidably disposed, for guiding the system into a vessel 2 blocked by a thrombus 4. The flexible guidewire is made slightly smaller than the channel to allow it to slide freely and the flexible piston is made slightly smaller than the flexible catheter to allow it to slide freely. However, blood leakage through these annular clearances is minimal because their small cross sectional area and their substantial length which makes the pressure drop along these clearances very gradual.

The proximal end of the flexible catheter is connected to an annular cavity 24 connected to a fluid port 26. A seal 28 seals the flexible catheter proximal end around the flexible piston.

Modification of the embodiment of FIGS. 1 and 2 is shown in FIGS. 3 and 3'. FIG. 3 shows the flexible catheter with a seal 30 which seals its around the flexible piston when the later extends distally from the flexible catheter allowing negative (or positive) pressure built up in the clearance between the flexible catheter and the flexible piston. The seal is opened when the piston is retracted into the flexible catheter. The flexible catheter is reinforced by a spiral winding 32 to stablilize its diameter and prevent it from collapsing because of mechanical or hydrostatic forces acting on it. FIG. 3' shows a simplified design where a guidewire means is integral with the flexible piston, extending from its distal tip. The guidewire means can be manufactured as a part of the flexible piston or the guidewire can be affixed to the flexible piston at a subsequent manufacturing step.

OPERATION

A process for removing a thrombus from a blood vessel, shown in FIG. 4, comprises the following steps:

Inserting a flexible guidewire into the vessel and advancing its distal end to the immediate vicinity of the thrombus, or across the thrombus, as shown in FIG. 5.

Inserting the system, over the flexible guidewire, into the vessel and advancing its distal end to the immediate vicinity of the thrombus, as shown in FIG. 6.

Pulling the proximal end of the flexible piston and sliding it proximally in the flexible catheter, thereby sucking the thrombus into the flexible catheter, as shown in FIG. 7. The piston is, preferably, withdrawn abruptly into the catheter, creating instantaneous vacuum at its distal tip. The sudden drop in pressure at the distal tip of the system helps to dislodge and suck the thrombus into the system.

Withdrawing the system containing the thrombus out of the vessel and clearing the vessel, as shown in FIG. 8.

Fluids, such as for example, thrombus dissolving drugs and radio opaque contrast material, can be introduced through the port and released through the flexible catheter distal end.

Alternatively, negative pressure may be applied to the port to assist the suction action created by retracting the flexible piston in the flexible catheter. When the modified design shown in FIG. 3 is used, the negative (or positive) pressure can be contained within the system until the flexible piston is retracted into the flexible catheter and the valve means 30 are opened.

While the present invention has been illustrated by limited number of embodiments, it should be understood that various modifications and substitutions may be made without departing from the spirit of the invention or the scope of the claims.

I claim:

1. A process for removing a thrombus from a blood vessel, comprising the following steps:
   inserting into the vessel a flexible thrombectomy system comprising a flexible piston, having proximal and distal ends, which is slidably disposed in a flexible catheter which also has proximal and distal ends,
   advancing the distal ends of the flexible piston and the flexible catheter to the immediate vicinity of the thrombus,
   pulling the proximal end of the flexible piston and sliding it proximally relative to the flexible catheter, thereby sucking the thrombus into the flexible catheter,
   withdrawing the system containing the thrombus out of the vessel.

2. A process for removing a thrombus, as in claim 1, wherein the flexible piston defines a channel for slidingly accommodating a flexible guidewire, and wherein,
   the flexible guidewire is advanced to the immediate vicinity of the thrombus, and,
   the flexible piston and the flexible catheter are advanced into the vessel over the flexible guidewire, prior to the sucking of the thrombus into the flexible catheter.

3. A process for removing a thrombus, as in claim 1, wherein fluid is introduced through the proximal end of the flexible catheter and released through the distal end of the flexible catheter.

4. A process for removing a thrombus, as in claim 1, wherein negative pressure is applied to the proximal end of the flexible catheter to assist the suction created by the pulling of the flexible piston relative to the flexible catheter.

5. A process for removing a thrombus, as in claim 1, wherein negative pressure is contained within the flexible catheter by valve means at the distal end of the system, the valve means adapted to open in response to the flexible piston being retracted into the flexible catheter.

* * * * *